United States Patent [19]
Cragg et al.

[11] Patent Number: 6,063,069
[45] Date of Patent: May 16, 2000

[54] METHOD AND APPARATUS FOR POWER LYSIS OF A THROMBUS

[75] Inventors: Andrew H. Cragg, Edina, Minn.; Edward L. Olson, Lake Forest, Calif.

[73] Assignee: Micro Therapeutics Inc., Irvine, Calif.

[21] Appl. No.: 09/079,487

[22] Filed: May 15, 1998

Related U.S. Application Data

[60] Provisional application No. 60/046,971, May 19, 1997.

[51] Int. Cl.$^7$ .................................................. A61M 31/00
[52] U.S. Cl. .............................. 604/508; 604/22; 604/523
[58] Field of Search ................................ 604/19, 22, 264, 604/523, 508

[56] References Cited

U.S. PATENT DOCUMENTS

| | | | |
|---|---|---|---|
| 3,841,308 | 10/1974 | Tate | 128/2 M |
| 4,370,982 | 2/1983 | Reilly | 604/98 |
| 4,661,094 | 4/1987 | Simpson | 604/53 |
| 4,795,439 | 1/1989 | Guest | 604/43 |

(List continued on next page.)

FOREIGN PATENT DOCUMENTS

| | | | |
|---|---|---|---|
| 0 470 781 A1 | 2/1992 | European Pat. Off. | A61B 17/22 |
| 3921071 A1 | 2/1991 | Germany | A61B 17/22 |
| 39 41 949 | 6/1991 | Germany | A61B 17/22 |
| 43 42 205 | 12/1994 | Germany | A61M 5/158 |
| WO 95/10232 | 4/1995 | WIPO | A61B 17/20 |
| WO 96/01079 | 1/1996 | WIPO | A61B 17/20 |

OTHER PUBLICATIONS

C. Werter MD et al., "Coronary Reperfusion with a New Catheter in Six Patients with Acute Occlusion After Angioplasty", *Cath. & Cardiovasc. Diag.*, 14:238–242 (1988).
Medi–Tech brochure "Products for Regional Thrombolysis", 7 pp., Nov. 1993.
Hicks M.D., Marshall E., "Multilevel Infusion Catheter for Use with Thrombolytic Agents", *JVIR*, 1991; 2:73–75.
"Pulse* Spray® Pulsed Infusion Systems", AngioDyamics® Nov. 1994 brochure (4 pp).
Bookstein M.D., Joseph J. et al., "Pulse–Spray Pharmacomechanical Thrombolysis", *Cardiovasc Intervent Radiol*, (1992) 15:228–233.
"EDM Infusion Catheter", Peripheral Systems Group brochure ©1989, (3 pp.).
McNamara M.D., Thomas et al., "Coaxial system improves thrombolysis of ischemia", *Diagnostic Imaging*, (Nov. 1991) pp. 122–131.

(List continued on next page.)

*Primary Examiner*—Corrine McDermott
*Attorney, Agent, or Firm*—Joseph F. Breimayer

[57] ABSTRACT

Thrombectomy methods and apparatus for removing a thrombus from a blood vessel involving high velocity injection of a thrombolytic agent, e.g., a plasminogen activator, through multiple, closely spaced, side wall infusion holes in a high strength catheter distal end infusion segment to lyse the adjacent thrombin. The infusion catheter is formed with a catheter lumen extending from a proximal end connector assembly to a distal end valve that is normally closed but is penetrable to allow introduction of a guidewire through the catheter lumen and distal end valve and to thereby allow advancement of the infusion catheter over the guidewire, thereby allowing access of the distal infusion segment to a wide number of locations. The infusion holes extend from the catheter lumen through the catheter side wall. Thrombolytic agent is pumped in a pulsatile manner through the catheter lumen under high pressure after removal of the guidewire and closure of the distal end valve. High velocity, short duration, power lysis jets are emitted through the closely spaced, small diameter infusion holes and finely lyse the thrombin without the need to withdraw blood and fibrin. The infusion segment is preferably moved back and forth as the power lysis jets of thrombolytic agent are emitted. The catheter infusion segment is moved to orient the infusion segment with successive sections of the thrombus, and the high velocity lysing is repeated as necessary.

34 Claims, 7 Drawing Sheets

U.S. PATENT DOCUMENTS

| | | | |
|---|---|---|---|
| 4,968,306 | 11/1990 | Huss et al. | 604/264 |
| 5,021,044 | 6/1991 | Sharkawy | 604/53 |
| 5,085,635 | 2/1992 | Cragg | 604/96 |
| 5,267,979 | 12/1993 | Appling et al. | 604/247 |
| 5,370,609 | 12/1994 | Drasler et al. | 604/22 |
| 5,370,653 | 12/1994 | Cragg | 606/170 |
| 5,399,158 | 3/1995 | Lauer et al. | 604/22 |
| 5,425,723 | 6/1995 | Wang | 604/280 |
| 5,474,530 | 12/1995 | Pasafaro et al. | 604/22 |
| 5,496,267 | 3/1996 | Drasler et al. | 604/22 |
| 5,505,729 | 4/1996 | Rau | 606/40 |
| 5,520,653 | 5/1996 | Reilly et al. | 604/152 |
| 5,536,242 | 7/1996 | Willard et al. | 604/30 |
| 5,554,114 | 9/1996 | Wallace et al. | 604/53 |
| 5,569,275 | 10/1996 | Kotula et al. | 606/159 |
| 5,957,901 | 9/1999 | Mottola et al. | 604/264 |

OTHER PUBLICATIONS

MeWisson M.D., Mark W. et al., Symptomatic Native Arterial Occlusions: Early Experience with "Over–the–Wire Thrombolysis", *JVIR*, 1990; 1:43–47.

Ritchie, J. L., et al., "Rotational approaches to atherectomy and thrombectomy", *Z. Kardiol.*, 76:Suppl. 6, 59–65 (1987).

Cragg M.D., Andrew H. et al., "New Developments in Thrombolytic Therapy", *Ninth Annual Int'l Symp. Vasc. Diag. & Interv.*, Jan. 27–30, 1997, pp. 83–86.

Bookstein M.D., Joseph J. et al., Pulse–Spray.

METHOD AND APPARATUS FOR POWER LYSIS OF A THROMBUS

This application claims the benefit of U.S. Provisional Application No. 60/046,971 filed May 19, 1997.

FIELD OF THE INVENTION

The present invention relates generally to thrombectomy methods and apparatus for removing a thrombus from a blood vessel or a medical device in or accessing a blood vessel, and more particularly to lysing and dissolving the thrombus through application of a fine spray or mist of a thrombolytic agent delivered to the thrombus at a high velocity from a plurality of infusion holes distributed around a relatively short infusion segment of an infusion catheter body.

BACKGROUND OF THE INVENTION

Thrombolytic agents including plasminogen activators and heparin compounds have been employed to dissolve blood clots or thrombi in native blood vessels and in vascular grafts and dialysis grafts. Such plasminogen activators include streptokinase, urokinase and tissue plasminogen activator (t-PA) and their analogues have been administered as lytic agents for lysis of arterial and venous thromboses.

A discussion of the prior art thrombectomy methods and apparatus for medically treating and removing a thrombus or blood clot in a blood vessel is set forth in U.S. Pat. No. 5,370,653 to Cragg, incorporated herein by reference, which discloses a thrombolytic brush method and apparatus for performing a thrombectomy. Attention is also directed to the article by A. H. Cragg M. D., entitled "New Developments in Thrombolytic Therapy" in *Ninth Annual International Symposium on Vascular Diagnosis and Intervention*, January 27–30, 1997, pp. 83–86, for a discussion of various thrombolytic therapies including the thrombolytic brush to effect a combination of pharmocologic and mechanical lysis. Various other infusion and pulse lytic catheter therapies for accomplishing arterial and venous lysis and to preserve the patency of a thrombosed dialysis access are also described.

One of the described therapies involves "weep" infusion of the thrombolytic agent through a plurality of infusion holes in an infusion segment of a coiled catheter of the type disclosed in U.S. Pat. No. 5,554,114 to Wallace et al. or of a straight catheter having a penetrable distal "valved-tip" for allowing advancement of the catheter over a guidewire as disclosed in U.S. Pat. No. 5,085,635 to Cragg, incorporated herein by reference. In this technique, thrombolytic agent is delivered at a constant low pressure through the catheter lumen and out of the infusion holes over a prolonged period of time. This approach has been used to provide weep infusion treatment of an elongated Deep Vein Thrombosis (DVT) as also described by N. H. Patel M. D. in the publication "Deep Vein Thrombolysis", by Micro Therapeutics, Inc. As described therein, urokinase infusion at 250,000 units/hour was delivered for 30 hours followed by a reduced volume of infusion delivery for another 7 hours to dissolve an elongated DVT in a patient suffering from a number of illnesses. While treatment of this nature is quite promising, it is costly due to the time that the patient is hospitalized and the amount of thrombolytic agent that is infused. In this case, more than 7,500,000 units of urokinase was infused to treat this patient.

Reference is also made in the above-referenced Cragg article to the article by J. J. Bookstein M. D. et al. entitled "Pulse-Spray Pharmocomechanical Thrombolysis", *Cardiovascular Interventional Radiology*, (1992) 15:228–233. The pulse spray system is also disclosed in the "Pulse*Spray® Pulsed Infusion System" literature of E. Z. EM, Inc. (© ANGIODYNAMICS® 11/94, 4 pp.) and in certain embodiments of U.S. Pat. No. 5,267,979 to Appling et al. In such pulse spray approaches, a catheter is used having a guidewire lumen extending to an open distal end allowing it to be introduced over a previously positioned guidewire to position a distal infusion pattern into a thrombus. In order to close the open distal end of the lumen, it is necessary to leave the guidewire in the lumen, which decreases the open cross-section and capacity of the catheter lumen to receive thrombolytic agent. The thrombolytic agent is injected into a side port of the proximal end assembly while the open distal end is occluded. The thrombolytic agent is ejected from the catheter lumen through a number of slits through the side wall of the catheter that are arranged in a circumfluent pattern in an infusion segment. Ejection of the thrombolytic agent through the slits is effected by manually expelling it from a 10 cc or smaller syringe and into the catheter lumen as described in the Bookstein et al. article and shown in FIG. 2 of the article. The thrombolytic agent is manually ejected at relatively low pressure and velocity from the slits. The manual injection procedure is repeated at about one or two pulses per minute intervals for about an average 20–35 minutes for lysing thrombi in dialysis grafts and about 60–120 minutes in the for lysing thrombi in a variety of vascular locations.

Attention is further directed to U.S. Pat. No. 5,370,609 to Drasler et al. disclosing a thrombectomy catheter device for axially applying one or more high pressure stream of sterile saline into a thrombus to emulsify the thrombus and propel the emulsion proximally through a catheter lumen for disposal. One of the high pressure streams is provided to establish a flow that draws the thrombus into the path of the other high pressure stream to emulsify it and then directs the fragments proximally through an evacuation lumen for disposal outside the patient's body.

A mechanical thrombus maceration catheter device is disclosed in U.S. Pat. No. 5,569,275 to Kotula et al. At least one impeller at the distal end of a drive shaft and located within a distal end housing is rotated at high speed, and the thrombus is macerated by the rotor as the distal end housing is advanced through it, and the macerated blood and thrombus fibrin particles are suctioned out of the blood vessel through a catheter lumen.

A further method of lysing thrombi employing the application of plasminogen activators in conjunction with pulsed mode ultrasound energy is disclosed in U.S. Pat. No. 5,399,158 to Laur et al.

In general, in approaches involving withdrawal of blood and fibrin particles, a great deal of blood may be withdrawn and need to be replaced, which is undesirable. Moreover, the axially directed fluid jets and the impeller maceration bores holes through thrombi, but can leave remnants behind adhering to the vessel wall or breaking free to flow away. The weep and pulse spray techniques and apparatus consume a great deal of expensive thrombolytic agent and a prolonged treatment of the patient which both add to the cost of the procedure. Despite these improvements in the art, a need remains for more rapid, efficacious, and less traumatic methods and apparatus for arterial, venous and vascular access lysis of thrombi, particularly DVTs.

SUMMARY OF THE INVENTION

The present invention relates to a number of approaches to satisfying these needs to shorten the time spent and to lower the amount of thrombolytic agent consumed and cost of treating such thrombi and to avoid the need to consume the patient's blood in the process.

In one embodiment of the invention, a selected bolus volume of thrombolytic agent, e.g., a plasminogen activator (e.g., urokinase), is injected at a selected flow rate into a high strength catheter lumen. The corresponding bolus volume is ejected or emitted through multiple side wall perforations or infusion holes closely spaced from one another in a relatively short infusion segment as high velocity, low volume, power lysis jets to lyse the adjacent thrombin. The high velocity, power lysis, jets relatively rapidly and finely lyse the thrombus without the need to withdraw blood and fibrin. The catheter infusion segment is advanced through the thrombus in the vessel, and the high velocity lysing is repeated as necessary to dissolve an elongated thrombus, e.g. a DVT.

The fine, high velocity, power lysis, jets result from the injection of a bolus of thrombolytic agent having a prescribed fluid density at a selected pressure and injection rate of flow (volume per unit of time) into the catheter lumen which is controlled by a power injector. The outflow rate of thrombolytic agent from the infusion holes is proportional to the total number and size (i.e., the total outflow area) of the infusion holes in the infusion segment, the pressure applied to the bolus as it is injected, and other factors. The injected bolus of thrombolytic agent injected into the catheter lumen forces a corresponding fraction of the bolus through each infusion hole. The ejection velocity of the power lysis jets is related to the outflow rate and inversely proportional to the total outflow area. The outflow rate is selected to maximize the velocity of the high velocity, power lysis, jets of thrombolytic agent while maintaining the force of the jets below a force that would be sufficient to damage the blood vessel wall.

The infusion holes are dense in the infusion segment, and the infusion segment is relatively short, between 0.2 cm to 2.0 cm long, to provide a "scrubbing" action of the closely spaced power lysis jets of the surrounding thrombin. For example, in one embodiment, 30 to 50 infusion holes are preferably provided per centimeter of length of the infusion segment and are evenly distributed around the circumference of the catheter body in each such cm of length. In another embodiment, the 20 to 32 infusion holes per linear centimeter are distributed in a helical pattern extending around the infusion segment and are closely spaced from one another. The high density spray of high velocity, power lysis jets causes the section of thrombus surrounding the short, 0.2 cm to 2.0 cm long, infusion segment to be thoroughly lysed and rapidly dissolved.

In use, the thrombolytic agent includes a diluted plasminogen activator and a radiopaque material that can be observed under fluoroscopy as it is emitted from the infusion holes as fine, high velocity, power lysis, jets. The catheter infusion segment can be advanced back and forth by the physician within the section of the thrombus during the emission of the power lysis jets to more evenly contact and lyse the section of the thrombus. The dissolution of the thrombus can be observed under fluoroscopy as the mixture displaces the thrombin from the blood vessel.

A number of advantages flow from the present invention. The present invention provides for a rapid dissolution of a thrombus, e.g. a DVT, thereby decreasing stress of the patient and time expended by the physician. The practice of the present invention infuses far less thrombolytic agent than is infused in the weeping and pulse spray approaches, thereby decreasing infusate cost significantly. The over-the-wire introduction of the catheter is simple and allows access to a wide number of locations, e.g. through the abdominal aorta, the iliac, femoral popliteal and tibial vessels. The valves of the leg veins are not damaged in the process of removing thrombi from leg veins. The catheter employed is relatively inexpensive and disposable.

BRIEF DESCRIPTION OF THE DRAWINGS

These and other objects, advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS

Figure 1:
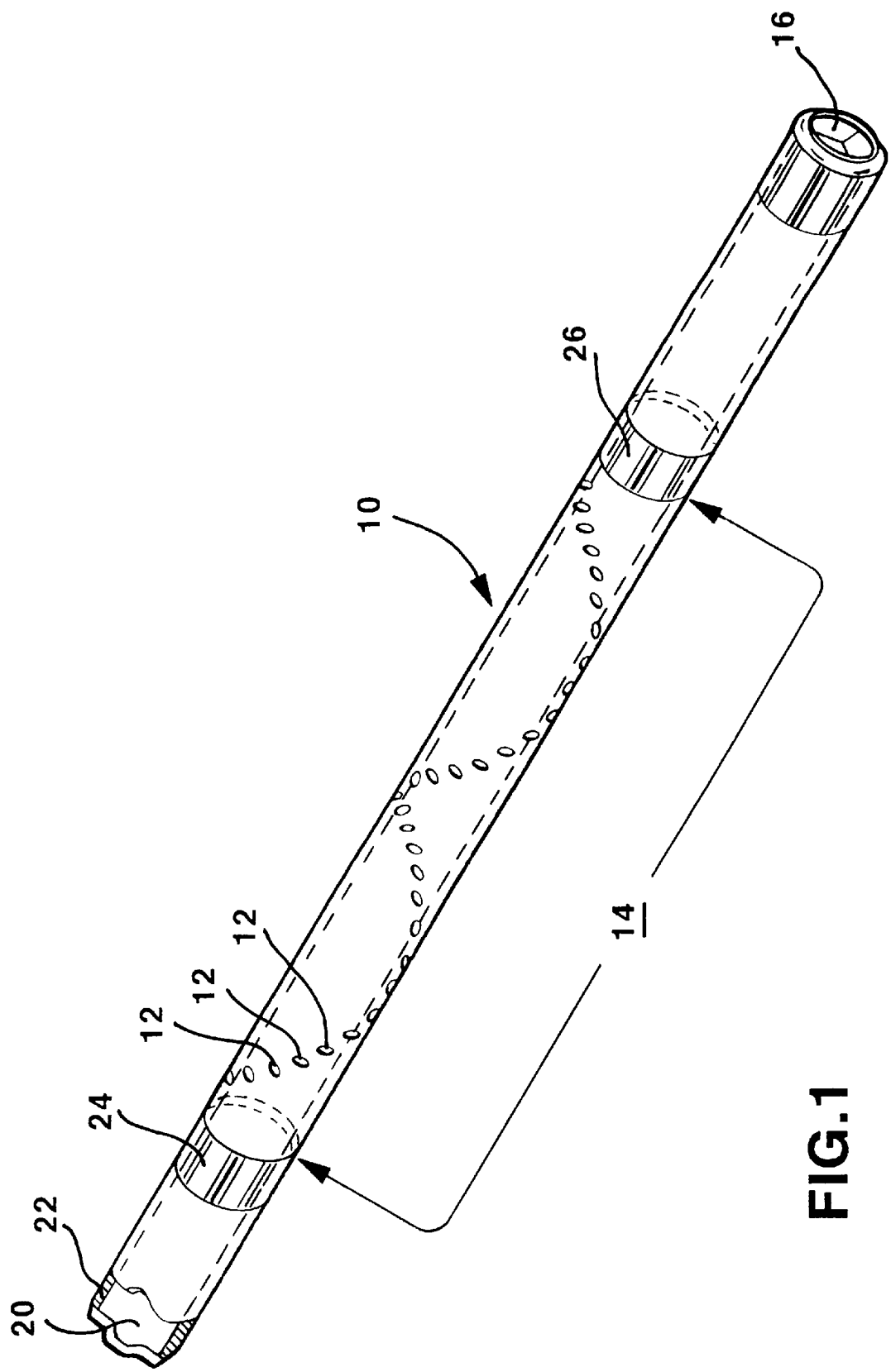
FIG. 1 is a perspective view of a power lysis catheter in accordance with a first embodiment of the present invention having a helical pattern of side wall infusion holes formed in the distal infusion segment.

In a preferred embodiment of the invention, a distal end section of an infusion catheter 10 is devised as shown in FIG. 1 for delivering a thrombolytic agent, e.g. a plasminogen activator, through a catheter lumen and from a plurality of side wall perforations or infusion holes 12 along a distal end infusion segment 14 just proximal to a distal end valve 16. The valve 16 is of the type described in above-incorporated U.S. Pat. No. 5,085,635 that closes the distal end of the catheter lumen 20 and is penetrable by a guidewire (not shown). The catheter lumen 20 extends the length of the infusion catheter 10 from a connector assembly at its proximal end (not shown) of a type known in the art to the distal infusion segment 14 and the distal end valve 16. A guidewire (not shown) can be inserted through the catheter lumen 20 and through the distal end valve 16 to allow over the wire placement of the distal end infusion segment 14 in relation to a thrombus in a blood vessel, graft or other device. The proximal connector assembly is intended to be in fluid communication with a source of plasminogen activator based, thrombolytic agent. The plurality of infusion holes 12 in the infusion segment 14 allows the thrombolytic agent to be delivered from the source through the infusion catheter lumen and to a thrombus surrounding it.

The infusion catheter 10 is formed with a side wall 22 that extends from the catheter lumen 20 to the catheter outer surface that is strong enough to withstand a relatively high pulsatile injection pressure applied from the source of thrombolytic agent to the thrombolytic agent that is injected into the catheter lumen 20. The side wall 22 may be formed of any of the known polymeric materials enclosing a reinforcing wire braid or material to withstand bursting under the fluid pressure applied to the thrombolytic agent within the catheter lumen 20. In one preferred embodiment, the outer diameter of the catheter 10 in the infusion segment 14 is about 0.166 cm, the side wall thickness is about 0.035 cm, and the lumen diameter is about 0.099 cm.

The distal infusion segment 14 preferably commences about 0.5 cm proximal from the distal end valve 16 and extends proximally for a relatively short length of about 0.2 cm to about 1 cm. Proximal and distal radiopaque marker bands 24 and 26 are preferably provided at the proximal and distal ends of the infusion segment 14 in order to identify its location using fluoroscopy.

The plurality of side wall infusion holes 12 are preferably arranged in a uniform or non-uniform pattern extending 360° around the catheter body in the distal infusion segment 14. The infusion holes 12 are preferably dense in the infusion segment 14, and the infusion segment 14 is relatively short. In the illustrated preferred embodiments of the invention, the plurality of infusion holes 12 are arranged in a spiral or helical pattern extending between the proximal and distal radiopaque marker bands 24 and 26. In this helical pattern, 20 to 32 infusion holes are preferably provided per cm of length of the infusion segment 14, depending on the pitch of the helical pattern.

The side wall perforations or infusion holes 12 are preferably about 0.01 cm (0.005 inches) in diameter. In FIG. 1, the infusion holes 12 are formed in a helical pattern that has a pitch determined by an offset of about 22.5° between adjacent infusion holes. Using a hole density of 32 holes per linear centimeter measured along the axial length of the infusion segment 14 results in a separation between adjacent holes along the helical pattern of about 0.03 cm (0.0125 inches). If the hole density is reduced to 20 per linear centimeter and the same pitch is maintained, then the separation between adjacent holes along the helical pattern is about 0.05 cm (0.020 inches).

The side wall perforations or infusion holes 12 are relatively minute, and their size meters the ejection of the plasminogen activator based, thrombolytic agent therethrough as fine, high velocity, power lysis jets for lysing the adjacent thrombus as illustrated in FIGS. 2–4 and 6–8. A bolus of thrombolytic agent is injected by a power injector into the proximal connector assembly and catheter lumen 20 at a predetermined pressure and rate as described below that pressurizes the thrombolytic agent in the catheter lumen 20 and forces the fine, high velocity, power lysis jets out of the infusion holes 12 in a spiral pattern.

Figure 2:
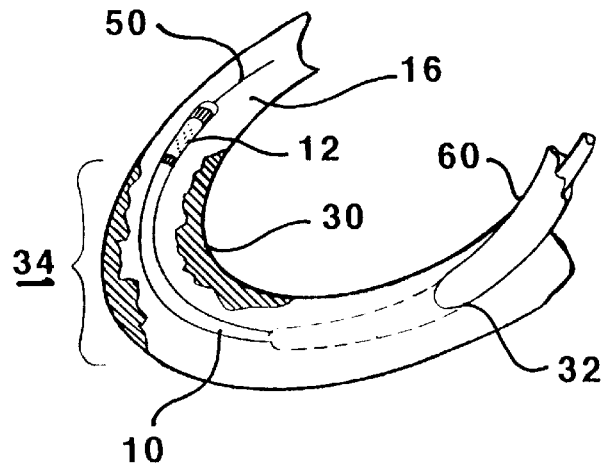
FIGS. 2–4 depict the use of the power lysis catheter to treat an elongated thrombus in a blood vessel.
Figure 3:
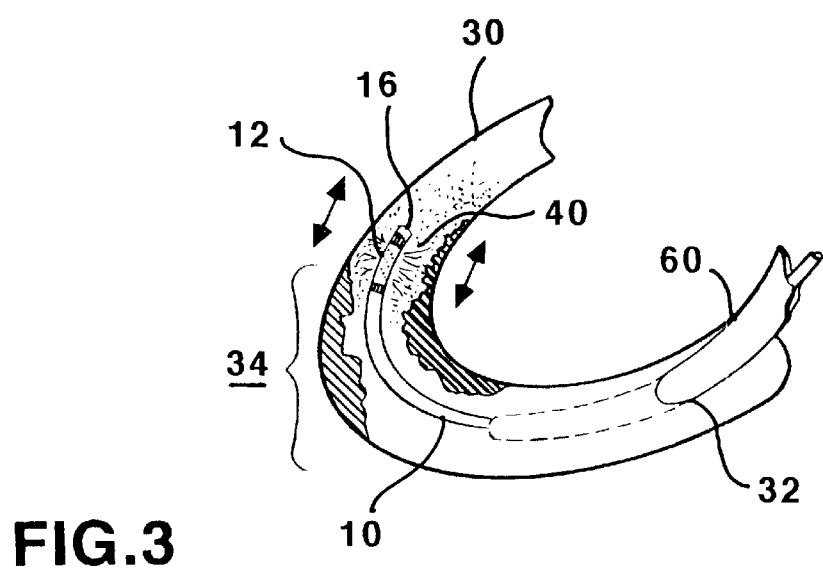
Figure 4:
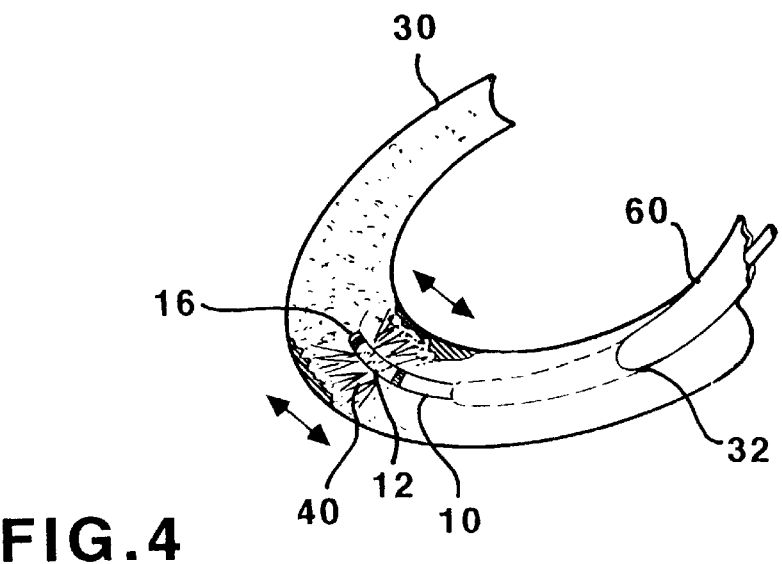

FIGS. 2–4 schematically illustrate steps in treating such an elongated thrombus 34 in a vein 30. In FIG. 2, the catheter 10 is advanced through an introducer 60 and over a guidewire 50, both previously advanced through an opening 32 in the patient's skin and the vein 30 that is distal to the distal end of the thrombus. The distal end valve 16 is penetrated by and slides over the guidewire 50 as the catheter 10 is advanced while being observed under fluoroscopy until the infusion segment 14 is located proximally past the proximal end of the thrombus 34. The guidewire 50 is retracted through the distal end valve 16 and the catheter lumen until it is removed from the connector end of the catheter 10 located outside the patient's body. The connector end of the catheter lumen is in fluid communication with a pulsatile fluid pump, e.g. a programmable power injector provided by Medrad, Inc., Indianola, Pa., under the trade name "Mark V" and Mark V Plus injection systems. These power injectors can be selectively adjusted to deliver an infusate from a source container into the lumen of a catheter at a selected flow rate and bolus volume or duration of each bolus. A limit can be set to limit the pressure of the infusate delivered into the catheter lumen, and the measured infusate pressure can also be displayed. Such power injectors are described in U.S. Pat. Nos. 4,370,982 and 5,520,653 to Reilly, for example.

In one example, 150 ml of a thrombolytic agent is prepared from a mixture of 250,000 units of urokinase, 40 ml of radiopaque contrast media, and the remainder of sterile saline for each 15 cm length (approximately) of the thrombus 34. The power injector is adjusted to deliver 5 ml of the thrombolytic agent to the catheter lumen at a rate of 25 ml/second. The power injector is set to a repeat mode to deliver the bolus at that rate once every 10 seconds, and the injection pressure of the mixture delivered into the catheter lumen is set to 600 psi. In FIG. 3, the power lysis jets 40 of the mixture are emitted in a spray extending in a spiral pattern around the infusion segment 14 in this embodiment employing infusion holes 12 arranged in a spiral pattern. It will be understood that the power lysis jets emitted by the more uniform pattern of infusion holes 12 of the first embodiment of FIG. 1 would form a somewhat more uniform spray. In either case, the back and forth movement of the catheter 10 by the physician tends to distribute the power lysis jets 40 within the surrounding section of the thrombus 34 to lyse it uniformly.

Then, in FIG. 3, the catheter 10 is retracted toward the opening 32 and into the proximal section of the thrombus 34. The physician optionally moves the catheter 10 back and forth slightly while each pulse of the thrombolytic agent is delivered. Progress in lysing the sections of the thrombus as the catheter 10 is moved is observed under fluoroscopy. The process continues to treat each section of the thrombus 34 as the catheter 10 is retracted toward the opening 32. It is expected that the 150 ml mixture will be consumed in thirty of the 5 ml pulsatile injections to treat a 20–30 cm length of thrombus over about a five minute time period. The mixture can be reloaded and the process continued for longer thrombus lengths.

At FIG. 4, the thrombus 34 is largely eliminated although fragments may remain attached to the blood vessel lumen wall. After completing this power lysis method, the catheter 10 is retracted from the blood vessel 30 through the lumen of the introducer 60. Finally, a post-lytic therapy regimen is followed to deliver a further quantity of thrombolytic agent over a longer period of time to completely dissolve the remaining fragments using a conventional infusion catheter of one of the types described above introduced into the lumen of the blood vessel 30. For example, a further quantity of thrombolytic agent is steadily delivered at a rate of 100,000 units per hour at low pressure from an IV pump along the length of the thrombus 34 for 12 hours while the patient rests.

In the use of the apparatus of the present invention as described above, the physician is able to see that the thrombus is being largely lysed as he/she manipulates the catheter 10 in FIGS. 3 and 4 and observes the fluoroscope. The lytic time spent by the physician is minimal, and the physician is afforded confidence that the treatment is working. The total time that the patient spends in the hospital or clinic during the lytic and post-lytic phases is about 12 hours which compares favorably to the 30 hours expended in the process described in the above-referenced Patel publication. In the example set forth above, the amount of thrombolytic agent is also reduced from more than 7,500,000 units in the above-referenced Patel publication to about 1,325,000 units for the 20–30 cm length thrombus. This reduction significantly reduces the total cost of the thrombolytic agent used in the treatment.

Figure 5:
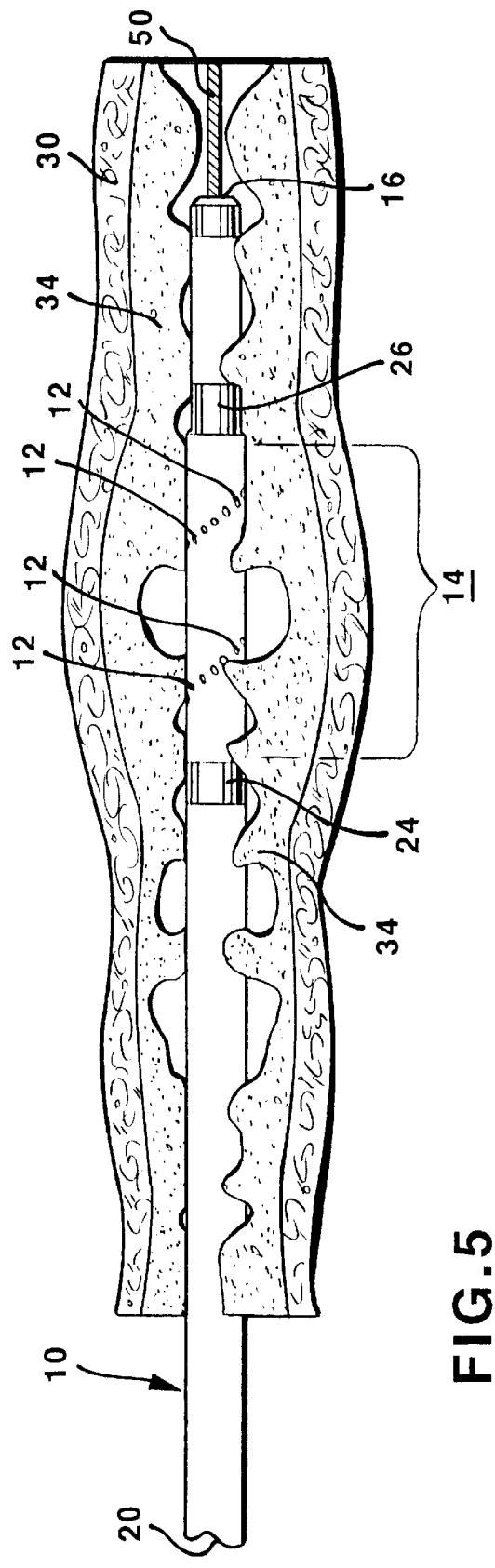
FIG. 5 is a more detailed view of the advancement of the infusion segment of the power lysis catheter over a previously placed guidewire into a thrombus section of an elongated thrombus in a blood vessel or medical device lumen.
Figure 6:
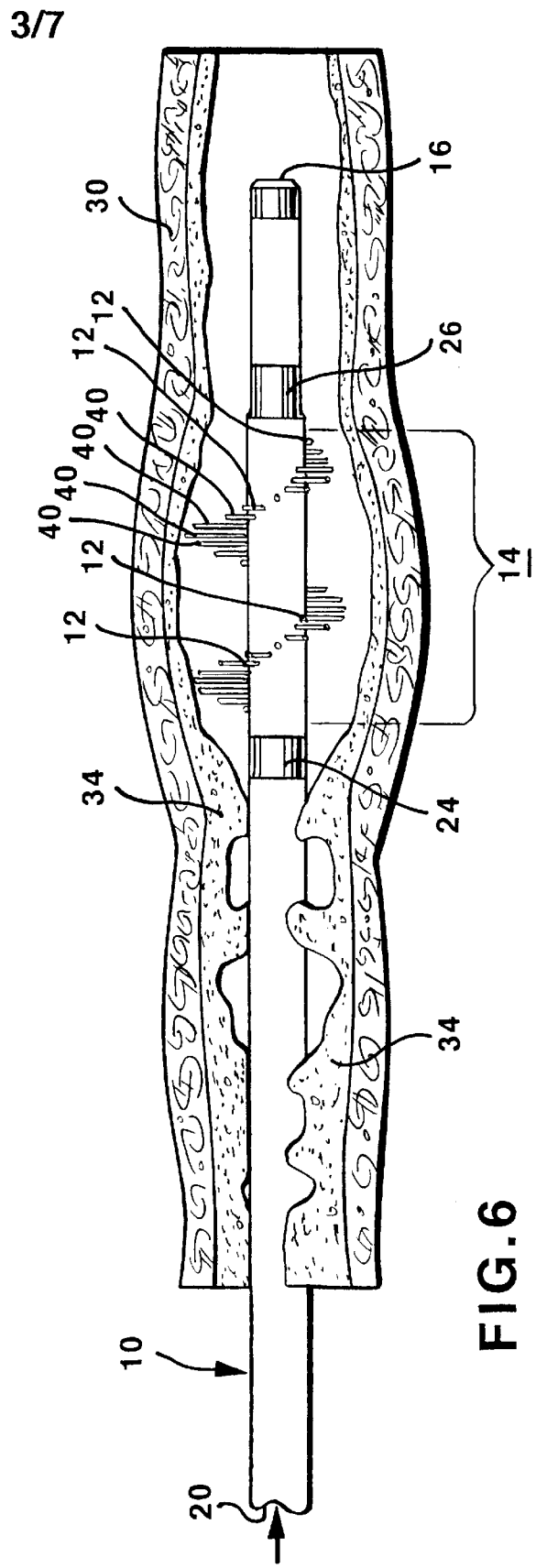
FIG. 6 is a view of the power lysis of the thrombus section of FIG. 5 with high velocity power lysis jets emitted after withdrawal of the guidewire from the catheter lumen and closure of the distal end valve.
Figure 7:
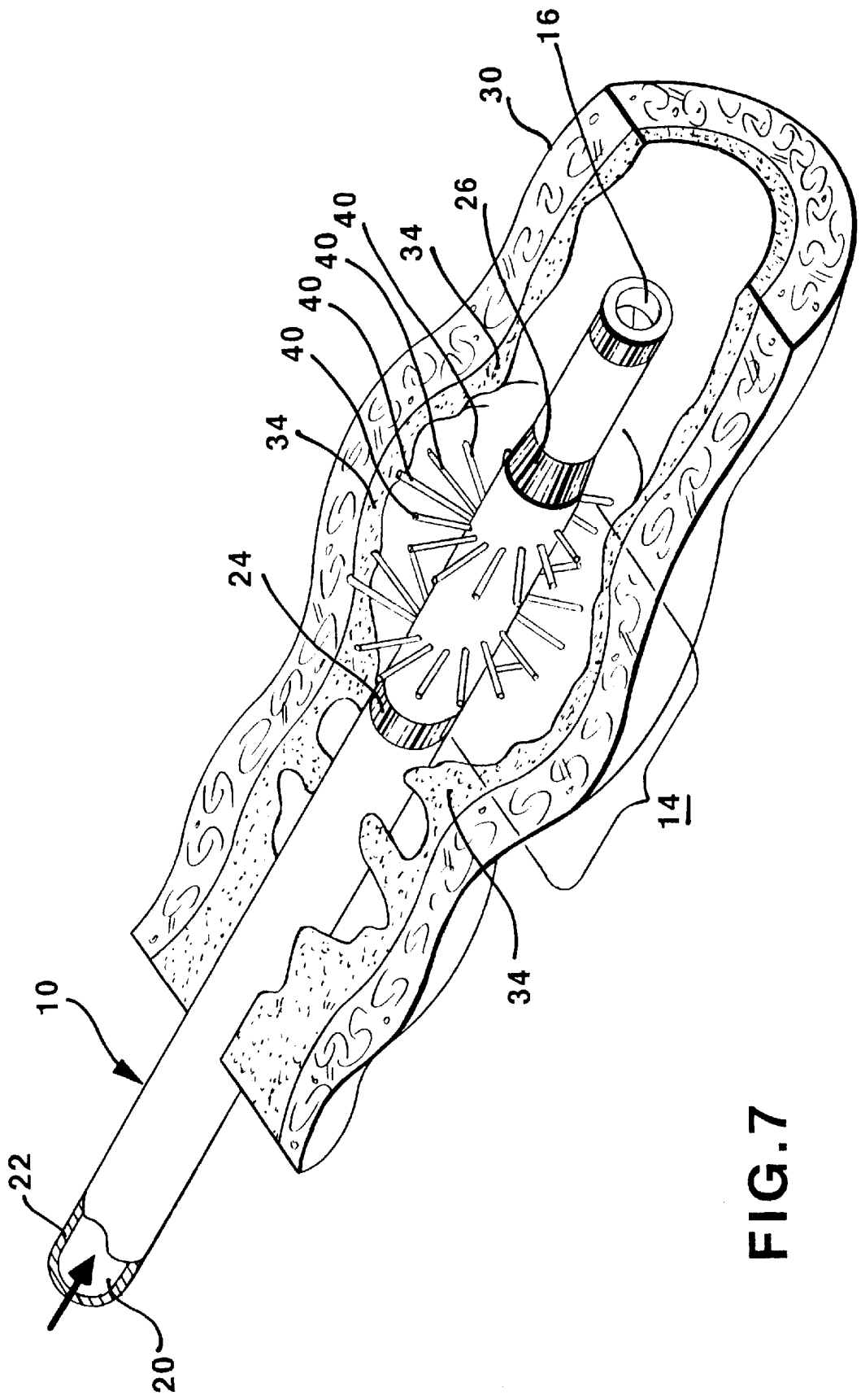
FIG. 7 is a perspective view of the pumping of thrombolytic agent from the infusion holes of the power lysis catheter to lyse the thrombus section of FIG. 5.
Figure 8:
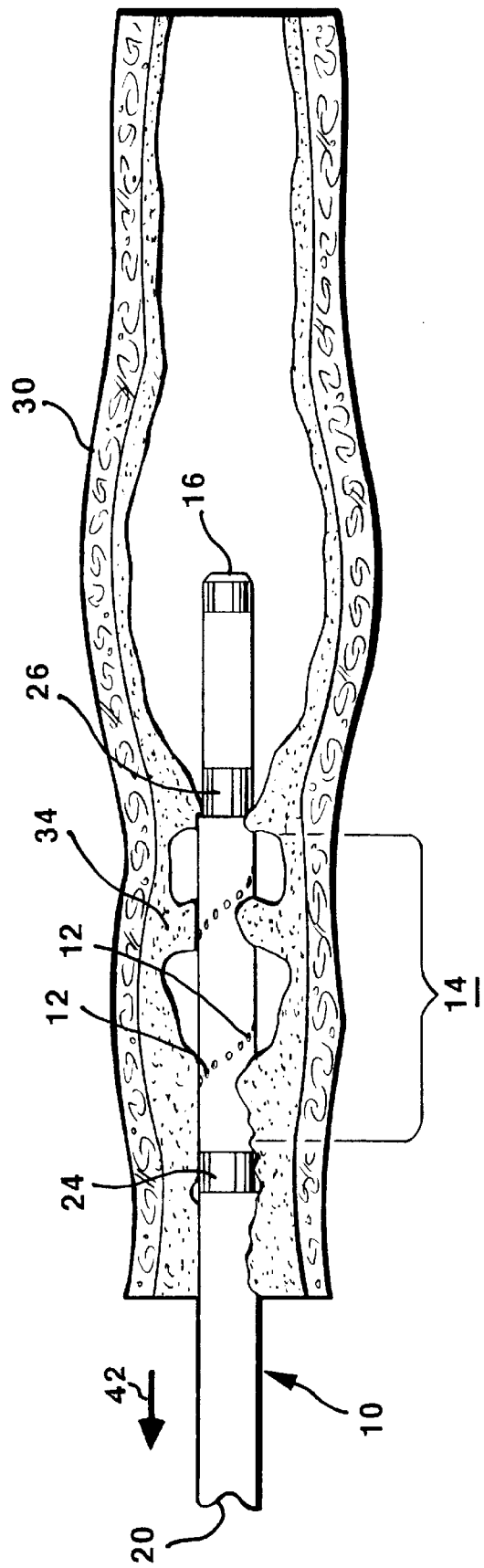
FIG. 8 is a more detailed view of the retraction of the infusion segment of the power lysis catheter over a previously placed guidewire into a more proximal thrombus section of the elongated thrombus to commence the power lysis of that section.

FIGS. 5–7 are more detailed views of the use of the power lysis catheter 10 to treat an elongated thrombus 34 in a blood vessel 30. In FIG. 5, the catheter 10 is advanced to the position of FIG. 3, and in FIG. 6, the power lysis jets 40 are injected into the section of thrombus 34 surrounding the infusion segment 14. FIG. 7 is a perspective view of the pumping of thrombolytic agent from the infusion holes 12 of the power lysis catheter 10 in power lysis jets 40 to lyse the thrombin in a thrombus section of an elongated thrombus 34 in a blood vessel 30. The catheter 10 is preferably moved back and forth slightly during the emission of the power lysis jets to more thoroughly contact and lyse the thrombus section. In FIG. 8, the catheter 10 is retracted in the direction of arrow 42 to the next adjacent section of the thrombus 34 to repeat the injection of FIG. 6.

Figure 9:
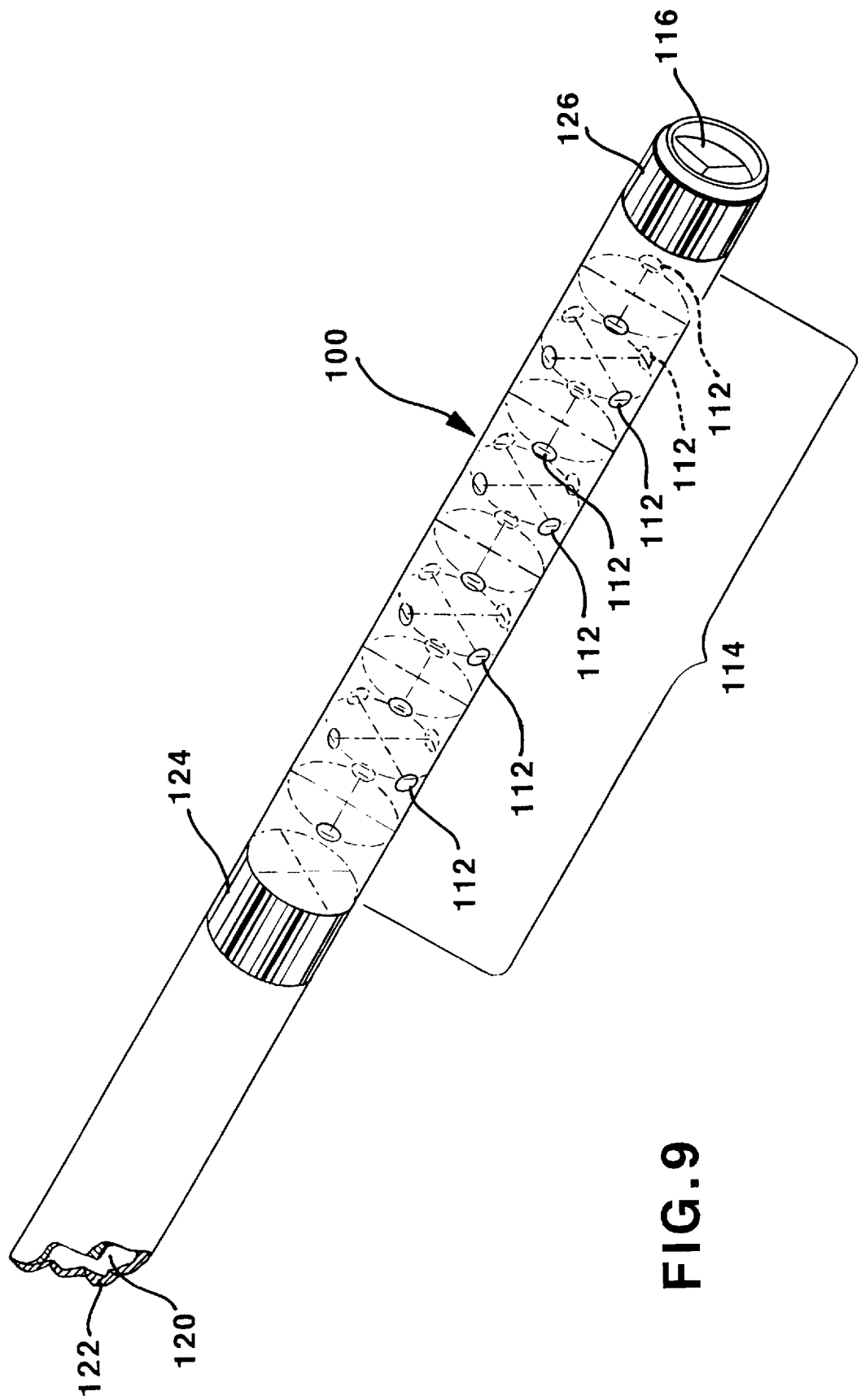
FIG. 9 is a perspective view of a power lysis catheter in accordance with a first embodiment of the present invention having a relatively uniform distribution of side wall infusion holes formed in the distal infusion segment.

FIG. 9 is a perspective view of a power lysis catheter 100 in accordance with a further embodiment of the present invention having a relatively uniform distribution of side wall infusion holes 112 formed in the distal infusion segment 114. In this embodiment, the infusion holes 112 are preferably evenly spaced apart and distributed along the length and 360° around the distal infusion segment 114 extending between proximal and distal radiopaque marker bands 124 and 126. In FIG. 9, for example, 30–50 side wall perforations or infusion holes 112 of about 0.01 cm (0.005 inches) in diameter may be formed per linear centimeter extending from the catheter lumen 120 through the catheter side wall 122. The plurality of side wall infusion holes 112 preferably extend proximally from about 0.5 cm from a distal end valve 116 for about 0.2 cm to 2.0 cm.

The infusion catheter 100 is otherwise constructed and used in the same manner as described above with reference to the infusion catheter 10. The infusion catheter 100 has at least one catheter lumen 120 extending the length thereof from a proximal end connector assembly (not shown) of a type known in the art to the distal end valve 116 that normally closes the distal end of the lumen catheter lumen 120. The distal end valve 116 is penetrable to allow a guidewire to be inserted through the lumen 120 and through the distal end valve 116 for over the wire placement of the distal end infusion segment 114 in relation to a thrombus (as shown in FIGS. 2 and 5 and described above). The catheter lumen 120 is also in fluid communication with a source of infusate at the proximal end of the catheter 100 for allowing the thrombolytic agent to be delivered therethrough and emitted through the plurality of infusion holes 112.

Figure 10:
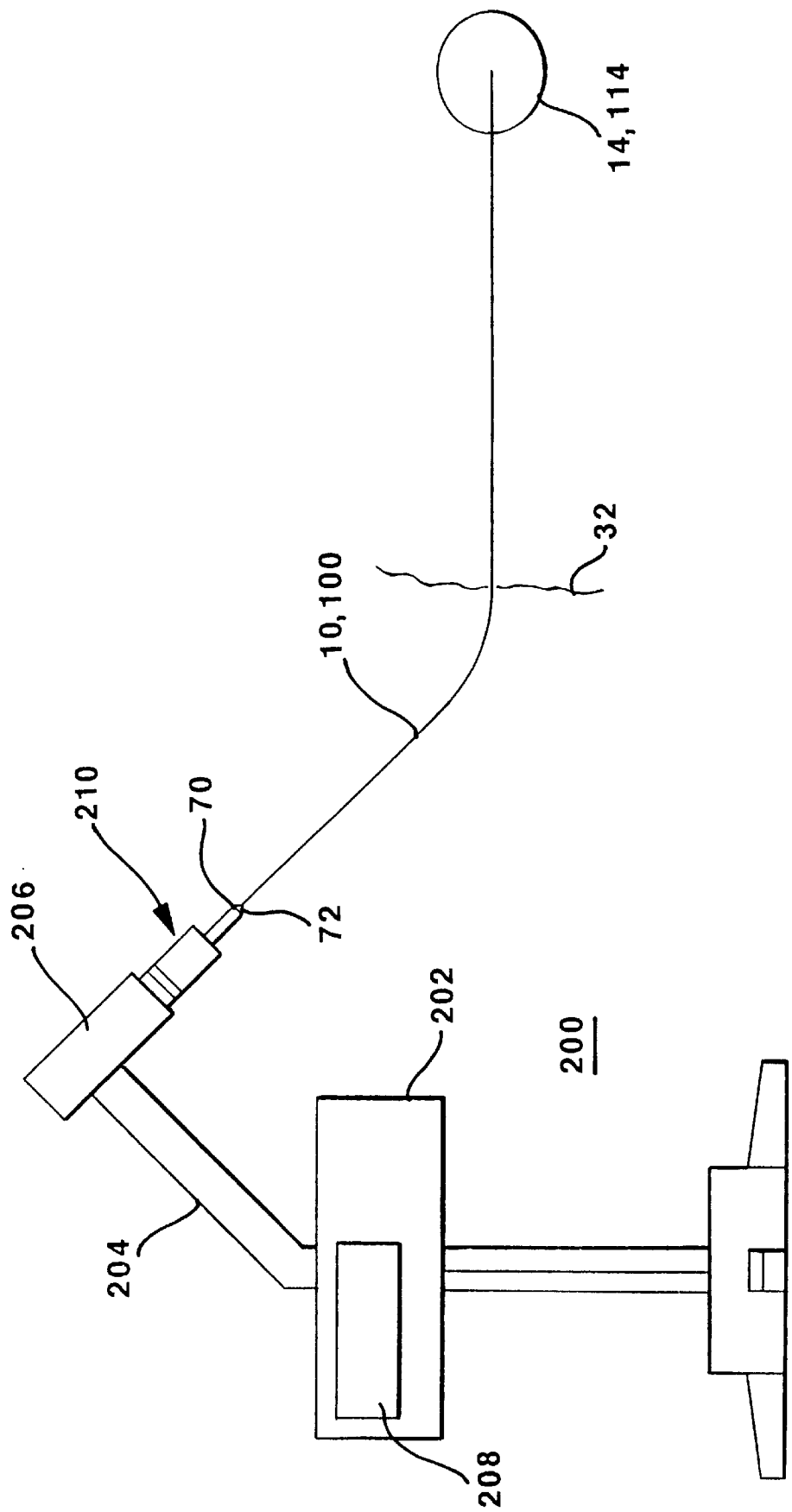
FIG. 10 is a simplified schematic illustration of a power lysis system for practicing the present invention.

FIG. 10 is a simplified schematic illustration of a pulsatile power injector system 200 e.g., the above-referenced power injector provided by Medrad, Inc., used with the preferred embodiments of the infusion catheter 10, 100 for practicing the methods of present invention. The system 200 includes a control console 202 that supports a pump or injector 206 and a thrombolytic agent supply or source 210 on an extended arm 204 enclosing control cables from the control console 202. A display and command entry panel 208 on the console 202 allows the user to enter the control commands and observe displayed data. The command entry panel 208 is used to select the thrombolytic agent pressure limit (in psi) within the catheter lumen, the volume of the bolus delivered (in ml) or the duration of delivery (in seconds), the rate of injection of the bolus (in ml/sec), the frequency of injection (times per minute). The power injector 206 is fitted with sensors for monitoring the thrombolytic agent pressure within the catheter lumen and the bolus volume that is pumped into the catheter lumen, and a feedback system controls both parameters. The proximal connector end assembly 70 at the proximal end 72 of the infusion catheter 10, 100 is coupled with the power injector 206 and the thrombolytic agent source 210.

In use of the depicted system 200, the catheter 10 or 100 is advanced through the access device in the opening 32 in the patient's skin and into the blood vessel or into the vascular device lumen and advanced over a previously introduced guidewire to the site of the thrombus as described above. The guidewire is withdrawn, and the catheter lumen 20 or 120 is filled with thrombolytic agent. The catheter lumen 20 or 120 is periodically pressurized as a bolus of thrombolytic agent is injected into the catheter lumen proximal end opening. A corresponding bolus of the thrombolytic agent is ejected through the plurality of infusion holes 12 or 112 during the time that the bolus is applied under pressure to the catheter lumen. The method steps illustrated in FIGS. 2–4 and 5–8 are followed.

The fine, high velocity, power lysis, jets result from the injection of a bolus of thrombolytic agent having a prescribed fluid density at a selected pressure and injection rate of flow (volume per unit of time) into the catheter lumen which is controlled by a power injector 200. The outflow rate of thrombolytic agent from the infusion holes 12, 112 is proportional to the total number and size (i.e., the total outflow area) of the infusion holes in the infusion segment 14, 114, the pressure applied to the bolus as it is injected, and other factors. The injected bolus of thrombolytic agent injected into the catheter lumen 20, 120 forces a corresponding fraction of the bolus through each infusion hole 12, 112. The ejection velocity of the power lysis jets is related to the outflow rate and inversely proportional to the total outflow area. The outflow rate is selected to maximize the velocity of the high velocity, power lysis, jets of thrombolytic agent while maintaining the force of the jets below a force that would be sufficient to damage the blood vessel wall.

The ejection velocity or power lysis jet velocity can be found utilizing the following total fluid outflow (Q) and velocity (v) equations:

$$Q = C_d A \sqrt{2 P_{ex}/\rho} \qquad (1)$$

and, after Q is determined using equation (1) or is determined out by the power injector:

$$v = Q/(C_c A) \qquad (2)$$

where:

$C_v$ is the velocity coefficient which approaches 0.8–0.9 for the thrombolytic agent mixture identified above;

$C_c$ is the contraction coefficient of the infusion hole (for example, $C_c \approx 0.60$–0.70 for a sharp edged aperture);

$C_d$ is the discharge coefficient $C_d = C_c \times C_v$ (or $\approx 0.54$ for example);

ρ is the fluid density (≈1.2 for the thrombolytic agent mixture described above);

$P_{ex}$ is the pressure head in excess of intervascular ambient pressure which is measured during delivery of the bolus and displayed by the power injector;

In practice, the total outflow Q is selected in ml/sec and the pressure head $P_{ex}$ is measured using the power injector 200. A power lysis jet velocity v of about 500–4000 inches/sec is calculated from these formulas using a pressure head $P_{ex}$ range of 30–900 psi and a total outflow area of about 0.25–0.50 mm².

The thrombolytic agent is delivered through the lumen of the catheter 10 at a pressure that well exceeds the pressure level employed in the above-described pulse-spray technique and is emitted through the infusion holes as relatively minute power lysis jets. These power lysis jets are sufficient to penetrate the thrombus but do not injure the vessel walls if they happen to contact the vessel walls. Moving the catheter back and forth slightly prevents a power lysis jet from dwelling too long in contact with a blood vessel and causes the contact with the thrombus to increase during the injection of each bolus of thrombolytic agent.

The thrombolytic agent is periodically pressurized at a higher frequency than once per minute as described in the above-referenced Bookstein et al. article so that the fine jets of thrombolytic agent are delivered more frequently. However, far less thrombolytic agent is delivered during each pulse and cumulatively over a comparable time period. The catheter 10 is advanced through the thrombus in the practice of the method of treating an elongated thrombus, e.g., an elongated DVT of the type described in the above-referenced Patel publication. As a result of these factors and techniques, the total time period of treatment is substantially shortened and the amount of delivered thrombolytic agent is substantially reduced.

The preferred embodiments of the invention may be employed to lyse a thrombus in a body blood vessel or in the blood flow lumen of an artificial graft, stent or vascular access device. In each case, the infusion segment is advanced into the thrombus, preferably in an over-the-wire procedure, and the thrombolytic agent is delivered as described above for each embodiment. The thrombolytic agent is delivered at high velocity in jets expelled outwardly of the catheter side walls, and the high velocity, power lysis jets lyse the adjacent thrombin of the thrombus.

The preceding specific embodiments are illustrative of the practice of the invention. It is to be understood, therefore, that other expedients known to those of skill in the art or disclosed herein may be employed without departing from the invention or the scope of the appended claims. It is therefore to be understood, that within the scope of the appended claims, the invention may be practiced otherwise than as specifically described without actually departing from the spirit and scope of the present invention.

What is claimed is:

1. A method of lysing a thrombus in a body vessel or artificial access device or the like comprising the steps of:

(a) providing an infusion catheter having a catheter lumen within an infusion catheter side wall extending between an outer surface and said catheter lumen, said infusion catheter and catheter lumen extending between a catheter proximal end and a catheter distal end, an elongated infusion segment formed of a plurality of spaced apart, infusion holes in said side wall that extend from said catheter lumen to the outer surface, the infusion holes having a diameter of about 0.01 cm and being provided at a density of at least 20 infusion holes in each centimeter of length of the distal infusion segment, and a valve in said catheter distal end that is normally closed to close said catheter distal end and penetrable by a guidewire for receiving said guidewire and allowing advancement of said infusion catheter over the guidewire;

(b) introducing a guidewire through the thrombus;

(c) advancing said infusion catheter over the guidewire to locate said elongated infusion segment thereof in relation with a section of the thrombus;

(d) removing the guidewire proximally from said valve to allow said valve to close;

(e) removing the guidewire proximally from said catheter lumen to allow said catheter lumen to be filled with a thrombolytic agent;

(f) orienting the infusion segment side wall of an infusion catheter with respect to a section of the thrombus;

(g) coupling a pulsatile fluid pump and a supply of thrombolytic agent to said catheter lumen at the catheter proximal end;

(h) periodically operating said pulsatile fluid pump to inject a predetermined bolus of thrombolytic agent from said supply into said catheter lumen at a predetermined injection pressure and injection rate to force the ejection of a plurality of fine power lysis jets of thrombolytic agent radially and outwardly of the infusion segment side wall at high jet velocity to mechanically penetrate the thrombus and to dissolve the penetrated thrombus by action of the ejected thrombolytic agent; and (i) repeating steps (f), (g) and (h) with respect to successive sections of the length of the thrombus to dissolve the sections of the thrombus.

2. The method of claim 1, wherein step (h) further comprises moving the elongated infusion segment with respect to the section of the thrombus during ejection of the power lysis jets to apply the power lysis jets to the section of thrombus.

3. The method of claim 2, wherein said spaced apart infusion holes are distributed over a length of the infusion segment of about 0.2 cm to about 2.0 cm in a density of 20–32 infusion holes per centimeter.

4. The method of claim 2, wherein step (h) further comprises injecting a bolus of about 5 ml of thrombolytic agent at a rate of about 25 ml per second into said catheter lumen at a pressure that effects ejection of a like bolus of thrombolytic agent through said plurality of infusion holes as said power lysis jets.

5. The method of claim 2, wherein step (h) further comprises injecting a bolus of about 5 ml of thrombolytic agent at a rate of about 25 ml per second into said catheter lumen at a pressure of about 30–900 psi that effects ejection of a like bolus of thrombolytic agent through said infusion holes and repeating the injecting step about once every 10 seconds.

6. The method of claim 2, wherein step (h) further comprises injecting a bolus of about 5 ml of thrombolytic agent at a rate of about 25 ml per second into said catheter lumen at a pressure of about 30–900 psi that effects ejection of a like bolus of thrombolytic agent through said infusion holes to achieve a power lysis jet velocity of about 500–4000 inches/sec.

7. The method of claim 1, wherein said spaced apart infusion holes are distributed over a length of the infusion segment of about 0.2 cm to about 2.0 cm in a density of 20–32 infusion holes per centimeter.

8. The method of claim 7, wherein step (h) further comprises injecting a bolus of about 5 ml of thrombolytic agent at a rate of about 25 ml per second into said catheter lumen at a pressure that effects ejection of a like bolus of thrombolytic agent through said plurality of infusion holes as said power lysis jets.

9. The method of claim 7, wherein step (h) further comprises injecting a bolus of about 5 ml of thrombolytic agent at a rate of about 25 ml per second into said catheter lumen at a pressure of about 30–900 psi that effects ejection of a like bolus of thrombolytic agent through said infusion holes and repeating the injecting step about once every 10 seconds.

10. The method of claim 7, wherein step (h) further comprises injecting a bolus of about 5 ml of thrombolytic agent at a rate of about 25 ml per second into said catheter lumen at a pressure of about 30–900 psi that effects ejection of a like bolus of thrombolytic agent through said infusion holes to achieve a power lysis jet velocity of about 500–4000 inches/sec.

11. The method of claim 1, wherein step (h) further comprises injecting a bolus of about 5 ml of thrombolytic agent at a rate of about 25 ml per second into said catheter lumen at a pressure that effects ejection of a like bolus of thrombolytic agent through said plurality of infusion holes as said power lysis jets.

12. The method of claim 1, wherein step (h) further comprises injecting a bolus of about 5 ml of thrombolytic agent at a rate of about 25 ml per second into said catheter lumen at a pressure of about 30–900 psi that effects ejection of a like bolus of thrombolytic agent through said infusion holes and repeating the injecting step about once every 10 seconds.

13. The method of claim 1, wherein step (h) further comprises injecting a bolus of about 5 ml of thrombolytic agent at a rate of about 25 ml per second into said catheter lumen at a pressure of about 30–900 psi that effects ejection of a like bolus of thrombolytic agent through said infusion holes to achieve a power lysis jet velocity of about 500–4000 inches/sec.

14. A method of lysing a thrombus in a body vessel or artificial access device or the like comprising the steps of:

(a) providing an elongated infusion catheter having an infusion catheter side wall defining an outer surface and enclosing an catheter lumen extending between a proximal catheter end and a distal infusion segment of the infusion catheter side wall, the infusion segment having a plurality of spaced apart, infusion holes in said side wall that extend from said catheter lumen to the outer surface, the infusion holes having a diameter of about 0.01 cm and being provided at a density of greater than 20 infusion holes in each centimeter of length of the distal infusion segment;

(b) advancing the elongated infusion catheter through a lumen of a blood vessel to extend the distal infusion segment within a thrombus of a blood vessel or vascular prosthesis;

(c) coupling a pulsatile fluid pump and a supply of thrombolytic agent to said catheter lumen at the catheter proximal end;

(d) introducing a thrombolytic agent into said catheter lumen at said proximal catheter end to fill said catheter lumen; and (e) periodically operating said pulsatile pump to introduce a predetermined bolus of infusate into said catheter lumen at a predetermined pressure to thereby eject a corresponding bolus of infusate through said plurality of spaced apart, infusion holes as a corresponding plurality of fine jets of thrombolytic agent radially outwardly of the infusion segment side wall at a high velocity to lyse the thrombus into particles as the thrombus is dissolved by the delivered thrombolytic agent.

15. The method of claim 14, wherein step (e) further comprises injecting a bolus of about 5 ml of thrombolytic agent at a rate of about 25 ml per second into said catheter lumen at a pressure that effects ejection of a like bolus of thrombolytic agent through said plurality of infusion holes as said power lysis jets.

16. The method of claim 14, wherein step (e) further comprises injecting a bolus of about 5 ml of thrombolytic agent at a rate of about 25 ml per second into said catheter lumen at a pressure of about 30–900 psi that effects ejection of a like bolus of thrombolytic agent through said infusion holes and repeating the injecting step about once every 10 seconds.

17. The method of claim 14, wherein step (e) further comprises injecting a bolus of about 5 ml of thrombolytic agent at a rate of about 25 ml per second into said catheter lumen at a pressure of about 30–900 psi that effects ejection of a like bolus of thrombolytic agent through said infusion holes to achieve a power lysis jet velocity of about 500–4000 inches/sec.

18. A method of lysing a thrombus in a body vessel or artificial access device or the like comprising the steps of:

(a) providing an elongated infusion catheter having an infusion catheter side wall defining an outer surface and enclosing an catheter lumen extending between a proximal catheter end and a distal infusion segment of the infusion catheter side wall, the infusion segment having a plurality of spaced apart, infusion holes in said side wall that extend from said catheter lumen to the outer surface;

(b) advancing the elongated infusion catheter through a lumen of a blood vessel to extend the distal infusion segment within a thrombus of a blood vessel or vascular prosthesis;

(c) coupling a pulsatile fluid pump and a supply of thrombolytic agent to said catheter lumen at the catheter proximal end;

(d) introducing a thrombolytic agent into said catheter lumen at said proximal catheter end to fill said catheter lumen; and (e) periodically operating said pulsatile pump to introduce a bolus of about 5 ml of thrombolytic agent at a rate of about 25 ml per second into said catheter lumen and through said plurality of spaced apart, infusion holes as a corresponding plurality of fine jets of thrombolytic agent radially outwardly of the infusion segment side wall at a high velocity to lyse the thrombus into particles as the thrombus is dissolved by the delivered thrombolytic agent.

19. The method of claim 18, wherein step (e) further comprises injecting the bolus of about 5 ml of thrombolytic agent at the rate of about 25 ml per second into said catheter lumen at a pressure of about 30–900 psi that effects ejection of a like bolus of thrombolytic agent through said infusion holes and repeating the injecting step about once every 10 seconds.

20. The method of claim 18, wherein step (e) further comprises injecting the bolus of about 5 ml of thrombolytic agent at the rate of about 25 ml per second into said catheter lumen at a pressure of about 30–900 psi that effects ejection of a like bolus of thrombolytic agent through said infusion holes to achieve a power lysis jet velocity of about 500–4000 inches/sec.

21. A system for lysing a thrombus in a body vessel or artificial access device or the like comprising:

an infusion catheter having a side wall and catheter lumen extending between a catheter proximal end and a catheter distal end, an elongated infusion segment having a plurality of closely spaced apart, infusion holes in said side wall that extend from said catheter lumen to the outer surface, the infusion holes having a diameter of about 0.01 cm and being provided at a density of at least 20 infusion holes in each centimeter of length of the distal infusion segment, and a valve in said catheter distal end that is normally closed to close the catheter lumen distal end and penetrable by a guidewire for receiving said guidewire and allowing advancement of said infusion catheter over the guidewire to orient the infusion segment side wall of an infusion catheter with respect to a section of the thrombus and for allowing withdrawal of the guidewire proximally from said valve to allow said valve to close and from said catheter lumen to allow said catheter lumen to be filled with a thrombolytic agent; and means for injecting a predetermined bolus of thrombolytic agent at a predetermined rate into said catheter lumen at a pressure that effects ejection at high velocity of a like bolus of thrombolytic agent through said infusion holes as fine power lysis jets of thrombolytic agent to mechanically penetrate the thrombus and to dissolve the penetrated thrombus by action of the ejected thrombolytic agent.

22. The lysing system of claim 21, wherein said injecting means further comprises a pulsatile fluid pump and a supply of thrombolytic agent coupled to said catheter lumen at the catheter proximal end.

23. The lysing system of claim 22, wherein said spaced apart infusion holes are distributed over a length of the infusion segment of about 0.2 cm to about 2.0 cm in a density of 20–32 infusion holes per centimeter length of said infusion segment.

24. The lysing system of claim 22, wherein said injecting means further comprises means for injecting a bolus of about 5 ml of thrombolytic agent at a rate of about 25 ml per second into said catheter lumen at a pressure that effects ejection of a like bolus of thrombolytic agent through said plurality of infusion holes as said power lysis jets.

25. The lysing system of claim 22, wherein said injecting means further comprises means operable about once every 10 seconds for injecting a bolus of about 5 ml of thrombolytic agent at a rate of about 25 ml per second into said catheter lumen at a pressure of about 30–900 psi that effects ejection of a like bolus of thrombolytic agent through said infusion holes.

26. The lysing system of claim 22, wherein said injecting means further comprises means for injecting a bolus of about 5 ml of thrombolytic agent at a rate of about 25 ml per second into said catheter lumen at a pressure of about 30–900 psi that effects ejection of a like bolus of thrombolytic agent through said infusion holes to achieve a power lysis jet velocity of about 500–4000 inches/sec.

27. The lysing system of claim 1, wherein said spaced apart infusion holes are distributed over a length of the infusion segment of about 0.2 cm to about 2.0 cm in a helical pattern in a density of 20–32 infusion holes per centimeter.

28. The lysing system of claim 27, wherein said injecting means further comprises means for injecting a bolus of about 5 ml of thrombolytic agent at a rate of about 25 ml per second into said catheter lumen at a pressure that effects ejection of a like bolus of thrombolytic agent through said plurality of infusion holes as said power lysis jets.

29. The lysing system of claim 27, wherein said injecting means further comprises means operable about once every 10 seconds for injecting a bolus of about 5 ml of thrombolytic agent at a rate of about 25 ml per second into said catheter lumen at a pressure of about 30–900 psi that effects ejection of a like bolus of thrombolytic agent through said infusion holes.

30. The lysing system of claim 27, wherein said injecting means further comprises means for injecting a bolus of about 5 ml of thrombolytic agent at a rate of about 25 ml per second into said catheter lumen at a pressure of about 30–900 psi that effects ejection of a like bolus of thrombolytic agent through said infusion holes to achieve a power lysis jet velocity of about 500–4000 inches/sec.

31. A system for lysing a thrombus in a body vessel or artificial access device or the like comprising:

an infusion catheter having a side wall and catheter lumen extending between a catheter proximal end and a catheter distal end, an elongated infusion segment having a plurality of closely spaced apart, infusion holes in said side wall that extend from said catheter lumen to the outer surface, the infusion holes having a diameter of about 0.01 cm and being provided at a density of greater than 20 infusion holes in each centimeter of length of the distal infusion segment, and a valve in said catheter distal end that is normally closed to close the catheter lumen distal end and penetrable by a guidewire for receiving said guidewire and allowing advancement of said infusion catheter over the guidewire to orient the infusion segment side wall of an infusion catheter with respect to a section of the thrombus and for allowing withdrawal of the guidewire proximally from said valve to allow said valve to close and from said catheter lumen to allow said catheter lumen to be filled with a thrombolytic agent; and means for injecting a bolus of about 5 ml of thrombolytic agent at a rate of about 25 ml per second into said catheter lumen at a pressure that effects ejection at high velocity of a like bolus of thrombolytic agent through said infusion holes as fine power lysis jets of thrombolytic agent to mechanically penetrate the thrombus and to dissolve the penetrated thrombus by action of the ejected thrombolytic agent.

32. The lysing system of claim 31, wherein said injecting means further comprises means for injecting the bolus of about 5 ml of thrombolytic agent at the rate of about 25 ml per second into said catheter lumen at a pressure of about 30–900 psi that effects ejection of a like bolus of thrombolytic agent through said infusion holes.

33. The lysing system of claim 31, wherein said injecting means further comprises means operable about once every 10 seconds for injecting the bolus of about 5 ml of thrombolytic agent at the rate of about 25 ml per second into said catheter lumen at a pressure of about 30–900 psi that effects ejection of a like bolus of thrombolytic agent through said infusion holes.

34. The lysing system of claim 31, wherein said injecting means further comprises means for injecting the bolus of about 5 ml of thrombolytic agent at the rate of about 25 ml per second into said catheter lumen at a pressure of about 30–900 psi that effects ejection of a like bolus of thrombolytic agent through said infusion holes to achieve a power lysis jet velocity of about 500–4000 inches/sec.

* * * * *